United States Patent
Nezhat et al.

(10) Patent No.: US 7,641,651 B2
(45) Date of Patent: Jan. 5, 2010

(54) DEVICES AND METHODS FOR MOBILIZATION OF THE UTERUS

(75) Inventors: Camran Nezhat, Woodside, CA (US); Joseph Eder, Los Altos Hills, CA (US)

(73) Assignee: Aragon Surgical, Inc., Palo Alto, CA (US)

( * ) Notice: Subject to any disclaimer, the term of this patent is extended or adjusted under 35 U.S.C. 154(b) by 639 days.

(21) Appl. No.: 11/193,881

(22) Filed: Jul. 28, 2005

(65) Prior Publication Data
US 2007/0027450 A1    Feb. 1, 2007

(51) Int. Cl.
*A61B 18/18*    (2006.01)
*A61B 18/14*    (2006.01)

(52) U.S. Cl. .............................. 606/32; 606/45; 606/48; 606/49; 606/50

(58) Field of Classification Search .................... 606/32, 606/37, 39–42, 48–50, 45
See application file for complete search history.

(56) References Cited

U.S. PATENT DOCUMENTS

| | | | |
|---|---|---|---|
| 3,709,215 A * | 1/1973 | Richmond | ................... 600/206 |
| 3,845,771 A | 11/1974 | Vise | |
| 3,920,021 A | 11/1975 | Hittenbrandt | |
| 4,041,952 A | 8/1977 | Morrison et al. | |
| 4,072,153 A | 2/1978 | Swartz | |
| 4,671,274 A | 6/1987 | Sorochenko | |
| 4,972,846 A | 11/1990 | Owens et al. | |
| 4,976,717 A | 12/1990 | Boyle | |
| 4,979,948 A | 12/1990 | Geddes et al. | |
| 5,037,379 A | 8/1991 | Clayman et al. | |
| 5,041,101 A | 8/1991 | Seder et al. | |
| 5,078,736 A | 1/1992 | Behl | |
| 5,108,408 A | 4/1992 | Lally | |
| 5,116,327 A | 5/1992 | Seder et al. | |
| 5,133,713 A | 7/1992 | Huang et al. | |
| 5,151,102 A | 9/1992 | Kamiyama | |
| 5,178,618 A | 1/1993 | Kandarpa | |
| 5,207,691 A | 5/1993 | Nardella | |
| 5,217,030 A | 6/1993 | Yoon | |
| 5,267,998 A | 12/1993 | Hagen | |
| 5,269,780 A | 12/1993 | Roos | |
| 5,269,782 A | 12/1993 | Sutter | |
| 5,281,216 A | 1/1994 | Klicek | |

(Continued)

OTHER PUBLICATIONS

Mansi Parikh, M. Rasmussen, L. Brubaker, C. Salomon, K. Sakamoto, R. Evenhouse, Z. Ai, and M. S. Damaser. Three Dimensional Virtual Reality Model of the Normal Female Pelvic Floor. Annals of Biomedical Engineering. 32:292-296, Feb. 2004.*

(Continued)

*Primary Examiner*—Lee S Cohen
(74) *Attorney, Agent, or Firm*—Michael A. Glenn; Glenn Patent Group

(57) ABSTRACT

An electrocautery device comprises first and second continuous loop electrode structures. The electrodes are typically coupled together at one end, permitting the electrodes to be introduced anteriorly and posteriorly over a uterine body. The electrodes may be clamped together, and radiofrequency energy may be delivered through the clamped electrodes to sever and cauterize blood vessels, tubular structures, and ligaments which connect the uterine body to surrounding tissue structures. The mobilized uterine body may then be removed by conventional hysterectomy.

13 Claims, 4 Drawing Sheets

U.S. PATENT DOCUMENTS

| | | |
|---|---|---|
| 5,282,799 A | 2/1994 | Rydell |
| 5,290,287 A | 3/1994 | Boebel et al. |
| 5,295,990 A | 3/1994 | Levin |
| 5,300,087 A | 4/1994 | Knoepfler |
| 5,324,289 A | 6/1994 | Eggers |
| 5,330,471 A | 7/1994 | Eggers |
| 5,336,229 A | 8/1994 | Noda |
| 5,336,237 A | 8/1994 | Chin et al. |
| 5,342,381 A | 8/1994 | Tidemand |
| 5,352,223 A | 10/1994 | McBrayer et al. |
| 5,352,235 A | 10/1994 | Koros et al. |
| 5,356,408 A | 10/1994 | Rydell |
| 5,391,166 A | 2/1995 | Eggers |
| 5,395,369 A | 3/1995 | McBrayer et al. |
| 5,396,900 A | 3/1995 | Slater et al. |
| 5,403,312 A | 4/1995 | Yates et al. |
| 5,417,687 A | 5/1995 | Nardella et al. |
| 5,423,814 A | 6/1995 | Zhu et al. |
| 5,443,463 A | 8/1995 | Stern et al. |
| 5,445,638 A | 8/1995 | Rydell et al. |
| 5,456,684 A | 10/1995 | Schmidt et al. |
| 5,458,598 A | 10/1995 | Feinberg et al. |
| 5,462,546 A | 10/1995 | Rydell |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,520,698 A | 5/1996 | Koh |
| 5,531,744 A | 7/1996 | Nardella et al. |
| 5,540,684 A | 7/1996 | Hassler, Jr. |
| 5,540,685 A | 7/1996 | Parins et al. |
| 5,542,945 A | 8/1996 | Fritzsch |
| 5,549,606 A | 8/1996 | McBrayer et al. |
| 5,558,100 A | 9/1996 | Cox |
| 5,558,671 A | 9/1996 | Yates |
| 5,569,243 A | 10/1996 | Kortenbach |
| 5,573,535 A | 11/1996 | Viklund |
| 5,578,052 A | 11/1996 | Koros et al. |
| 5,599,350 A | 2/1997 | Schulze et al. |
| 5,603,711 A | 2/1997 | Parins et al. |
| 5,611,803 A | 3/1997 | Heaven et al. |
| 5,624,452 A | 4/1997 | Yates |
| 5,637,110 A | 6/1997 | Pennybacker |
| 5,637,111 A | 6/1997 | Sutcu et al. |
| 5,653,692 A | 8/1997 | Masterson et al. |
| 5,658,281 A | 8/1997 | Heard |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt et al. |
| 5,674,184 A | 10/1997 | Hassler, Jr. |
| 5,674,220 A | 10/1997 | Fox et al. |
| 5,681,282 A | 10/1997 | Eggers et al. |
| 5,683,385 A | 11/1997 | Kortenbach |
| 5,683,388 A | 11/1997 | Slater |
| 5,688,270 A | 11/1997 | Yates et al. |
| 5,693,051 A | 12/1997 | Schulze et al. |
| 5,697,949 A | 12/1997 | Giurtino et al. |
| 5,700,261 A | 12/1997 | Brikerhoff |
| 5,702,390 A | 12/1997 | Austin et al. |
| 5,707,369 A | 1/1998 | Vatekunas et al. |
| 5,709,680 A | 1/1998 | Yates et al. |
| 5,713,896 A | 2/1998 | Nardella et al. |
| 5,718,703 A | 2/1998 | Chin |
| 5,733,283 A | 3/1998 | Malis et al. |
| 5,735,289 A * | 4/1998 | Pfeffer et al. ............... 600/564 |
| 5,735,848 A | 4/1998 | Yates et al. |
| 5,735,849 A | 4/1998 | Baden et al. |
| 5,741,285 A | 4/1998 | McBrayer |
| 5,743,906 A | 4/1998 | Parins et al. |
| 5,746,750 A | 5/1998 | Prestel et al. |
| 5,755,717 A | 5/1998 | Yates et al. |
| 5,833,690 A | 11/1998 | Yates et al. |
| 5,840,077 A | 11/1998 | Rowden et al. |
| 5,979,453 A | 11/1999 | Savage et al. |
| 6,059,766 A | 5/2000 | Greff |
| 6,059,782 A | 5/2000 | Novak et al. |
| 6,066,139 A | 5/2000 | Ryan et al. |
| 6,123,701 A * | 9/2000 | Nezhat ......................... 606/33 |
| 6,152,932 A * | 11/2000 | Ternstrom ................... 606/114 |
| 6,245,069 B1 | 6/2001 | Gminder |
| 6,254,601 B1 | 7/2001 | Burbank et al. |
| 6,334,861 B1 | 1/2002 | Chandler et al. |
| 6,494,881 B1 | 12/2002 | Bales et al. |
| 6,546,933 B1 | 4/2003 | Yoon |
| 6,602,251 B2 | 8/2003 | Burbank et al. |
| 6,743,229 B2 | 6/2004 | Buysse et al. |
| 6,746,488 B1 | 6/2004 | Bales |
| 6,764,488 B1 | 7/2004 | Burbank et al. |
| 6,905,506 B2 | 6/2005 | Burbank et al. |
| 6,926,712 B2 | 8/2005 | Phan |
| 7,033,356 B2 | 4/2006 | Latterell et al. |
| 7,094,235 B2 | 8/2006 | Francischelli |
| 7,169,146 B2 | 1/2007 | Truckai et al. |
| 7,179,254 B2 | 2/2007 | Pendekanti et al. |
| 2001/0014805 A1 | 8/2001 | Burbank et al. |
| 2002/0124853 A1 | 9/2002 | Burbank et al. |
| 2004/0199161 A1 | 10/2004 | Truckai et al. |
| 2005/0033276 A1 | 2/2005 | Adachi |
| 2005/0070895 A1 * | 3/2005 | Ryan et al. .................... 606/48 |
| 2005/0096645 A1 | 5/2005 | Wellman et al. |
| 2005/0107781 A1 | 5/2005 | Ostrovsky et al. |
| 2005/0256524 A1 | 11/2005 | Long et al. |
| 2005/0261676 A1 | 11/2005 | Hall et al. |
| 2006/0025765 A1 * | 2/2006 | Landman et al. .............. 606/48 |

OTHER PUBLICATIONS

Kovac; "Transvaginal Hysterectomy: Rationale and Surgical Approach"; 2004; Obstetrics and Gynecology; 103: 1321-1325.
ERBE Elektromedizin GmbH; "ERBE BiClamp"; retrieved from the Internet on Nov. 15, 2004; http://www.erbe-med.com/BiClamp_e/BiClamp_thermofusion_e.html.
Gyrus Medical; "PK Seal"; retrieved online on Nov. 15, 2004 from: http://www.vitalmed.com/prducts/gyrus/gyrus_pk_seal.htm.
McClurken, et al.; "Collagen Shrinkage and Vessel Sealing"; 2001; Tissuelink Medical Inc. Technical Brief #300.
SAGES 2001 Nurses Program, Session 1, retrieved online on Nov. 15, 2004 from: http://sages.org/01program/syllabi/nurse/nurse.html.
SURGRX 510(K) Summary, Jul. 3, 2003, Palo Alto, California.
Treat, "A New Thermal Device for Sealing and Dividing Blood Vessels"; Jun. 29, 2005; retrieved on the internet from: http://www.starioninstruments.com/PDFs/Treat.pdf.
Tyco Healthcare, "The LigaSure Vessel Sealing"; Apr. 2002, 7 pages.

* cited by examiner

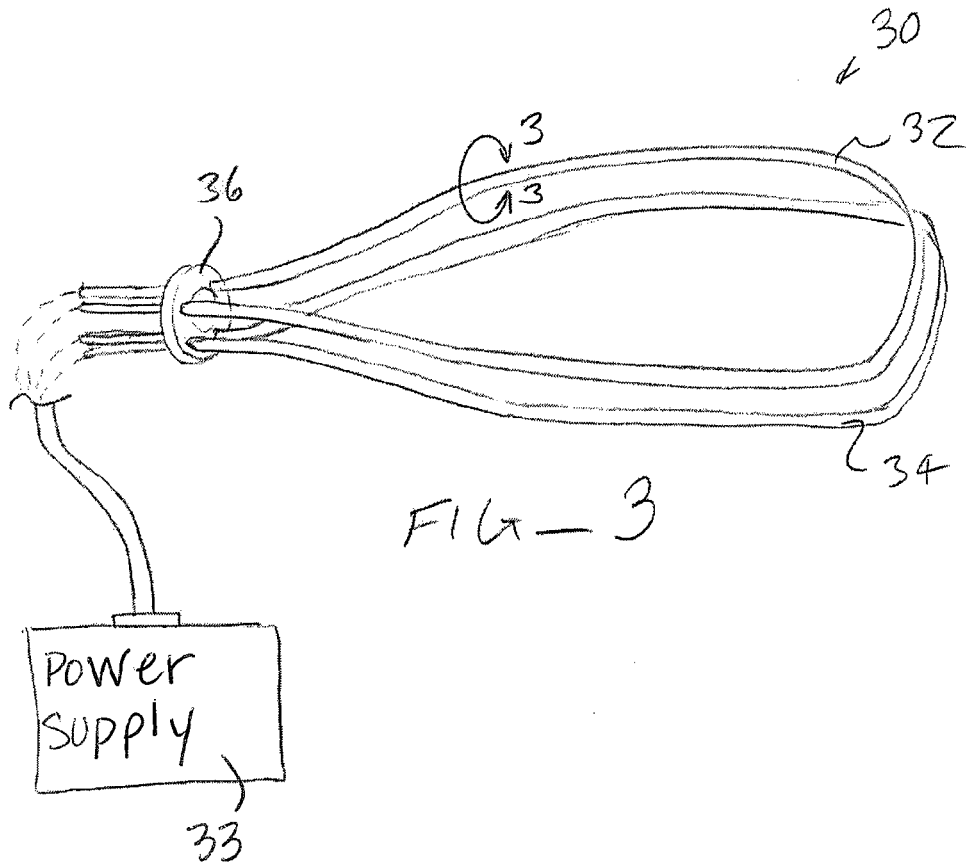
FIG_3
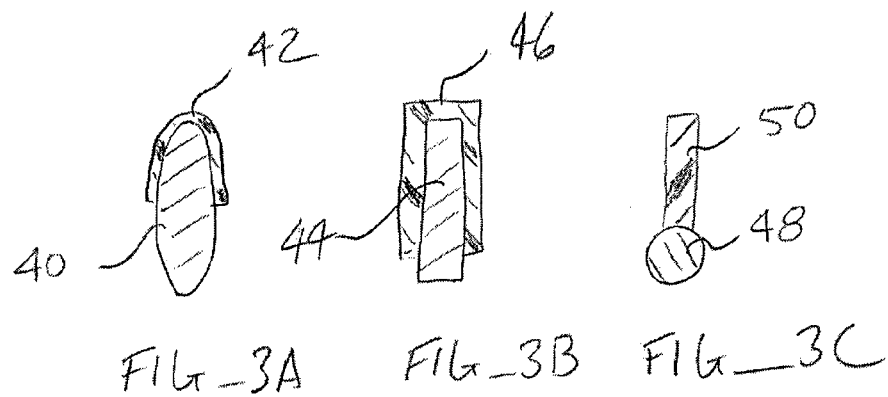
FIG_3A  FIG_3B  FIG_3C

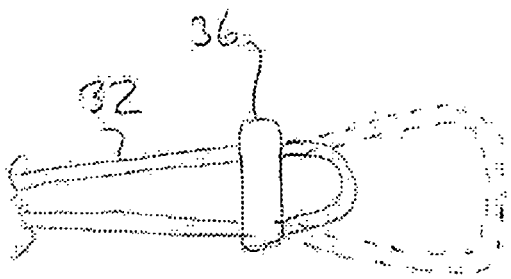
FIG_ 4A
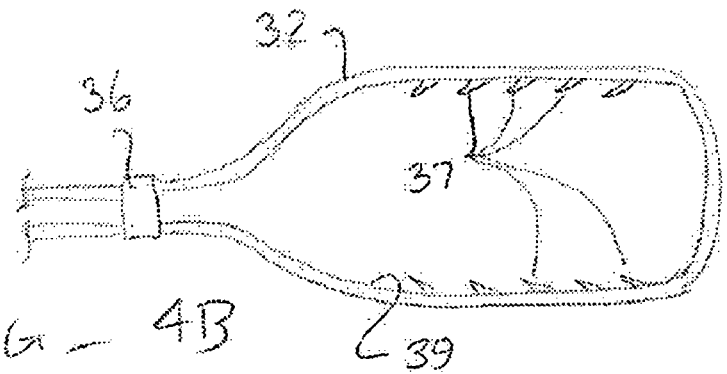
FIG_ 4B
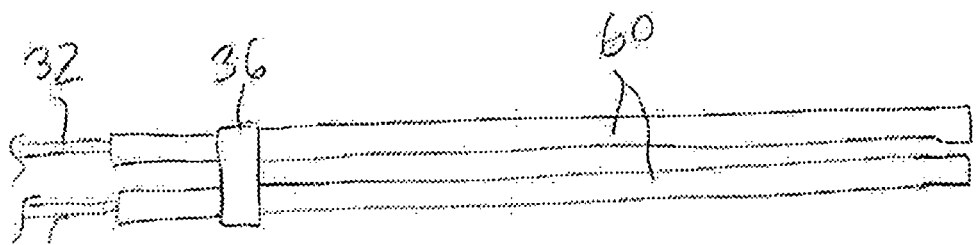
FIG_ 5A
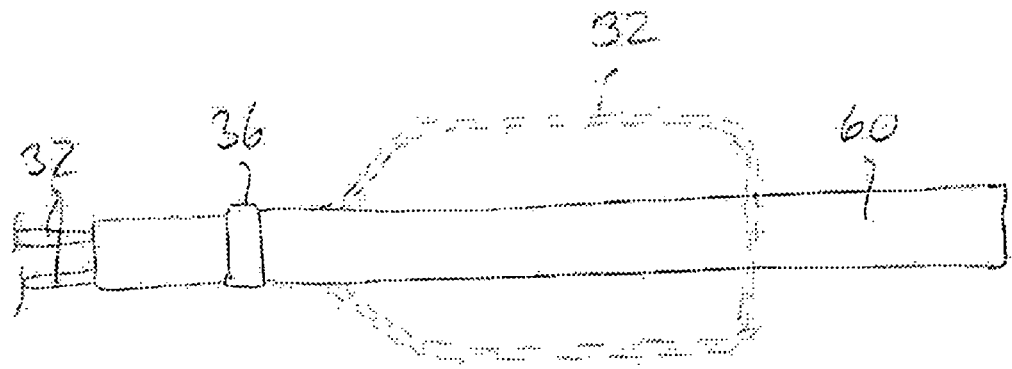
FIG_ 5B

DEVICES AND METHODS FOR MOBILIZATION OF THE UTERUS

BACKGROUND OF THE INVENTION

1. Field of the Invention

The present invention relates generally to medical devices and methods, and more particularly to methods and gynecological devices for mobilization of the female uterus prior to hysterectomy or other procedures.

Hysterectomy involves total or partial removal of the body and cervix of the uterus. Hysterectomy is one of the most common surgical procedures performed in the United States. By the age of sixty, nearly one in three American women will have undergone hysterectomy, and it is estimated that over a half million women undergo hysterectomy each year in the United States alone. The costs related to performing hysterectomies cost the United States healthcare system billions of dollars annually.

A majority of hysterectomies are performed by an open abdominal surgical procedure as surgeons have the most experience with this approach. An open abdominal surgical route allows for removal of a large sized uterus or other diseased organs or tissue, such as the ovaries, fallopian tubes, endometriosis, adenomyosis, and the like. However, open abdominal hysterectomy suffers from several drawbacks. The surgical procedure is often lengthy and complicated, requiring longer anesthesia periods and the increased risk of postoperative complications. Patients also suffer from prolonged recovery periods, pain and discomfort, and large visible scarring on the abdomen. Further, increased costs are associated with an open abdominal approach, such as prolonged hospital stays.

Two less invasive alternatives to performing hysterectomies are vaginal and laparoscopically assisted vaginal hysterectomy. A vaginal hysterectomy, which is of particular interest to the present invention, involves a surgical approach through the vaginal tubular tract to gain access directly to the uterus. Hysterectomies may also be performed with a range of laparoscopic assistance, often using a laparoscopic port for viewing only where all other steps are completed vaginally. Hysterectomies may be completely performed laparoscopically, typically requiring mobilization of the uterus and subsequent removal of the uterus through a laparoscopic port.

A problem common to both transvaginal and laparoscopic hysterectomies is the dissection of the uterus from the surrounding blood vessels, tubular structures, and ligaments which attach the uterus to surrounding tissue structures. In transvaginal procedures, it is often necessary to advance surgical blades, electrocautery elements or other dissection tools in a blind fashion in an effort to cut and seal the blood vessels, tubular structures, and ligaments. Even with laparoscopic viewing, such procedures for freeing the uterus from surrounding tissue structures are difficult.

For these reasons, it would be desirable to provide improved methods and apparatus for performing transvaginal and laparoscopic hysterectomies. In particular, it would be desirable to provide improved methods and apparatus for mobilizing the uterus by dissecting the blood vessels, tubular structures, and ligaments surrounding the uterus to free the uterus from surrounding tissue structures. Such improved methods and apparatus would desirably reduce procedure times and complexity, and result in improved patient outcomes while simultaneously reducing costs of the procedure. At least some of these objectives will be met by the inventions described hereinbelow.

2. Description of the Background Art

Electrosurgical cutting loops are described in U.S. Pat. No. 6,245,069. Methods and systems for organ resection are described in U.S. Pat. No. 6,123,701, licensed to the assignee of the present application and incorporated herein by reference. Bipolar forceps for coagulating blood vessels are described in U.S. Pat. No. 5,443,463. The use of radio frequency energy to necrose the endothelial lining of the uterus is described in U.S. Pat. No. 4,979,948. The following U.S. Patents may also be relevant to the present invention: U.S. Pat. Nos. 3,920,021; 3,845,771; 4,041,952; 4,671,274; 4,972,846; 5,037,379; 5,078,736; 5,151,102; 5,178,618; 5,207,691; 5,217,030; 5,267,998; 5,269,780; 5,269,782; 5,281,216; 5,282,799; 5,290,287; 5,295,990; 5,300,087; 5,324,289; 5,330,471; 5,336,229; 5,336,237; 5,342,381; 5,352,223; 5,352,235; 5,356,408; 5,391,166; 5,395,369; 5,396,900; 5,403,312; 5,417,687; 5,423,814; 5,445,638; 5,456,684; 5,458,598; 5,462,546; 5,482,054; 5,484,435; 5,484,436; 5,496,312; 5,496,317; 5,514,134; 5,531,744; 5,540,684; 5,540,685; 5,542,945; 5,549,606; 5,558,100; 5,558,671; 5,569,243; 5,573,535; 5,578,052; 5,599,350; 5,603,711; 5,611,803; 5,624,452; 5,637,110; 5,637,111; 5,653,692; 5,658,281; 5,665,085; 5,665,100; 5,667,526; 5,669,907; 5,674,184; 5,674,220; 5,681,282; 5,683,385; 5,683,388; 5,688,270; 5,693,051; 5,697,949; 5,700,261; 5,702,390; 5,707,369; 5,709,680; 5,713,896; 5,718,703; 5,733,283; 5,735,289; 5,735,848; 5,735,849; 5,741,285; 5,743,906; 5,755,717; 5,833,690; 6,743,229. The subject matter of this application is related to the following copending, commonly assigned applications: No. 60/680,937 (docket 025741-000100US); Ser. No. 11/137,970 (docket 025741-000300US); and Ser. No. 11/173,478 (docket 025741-000500US), the full disclosures of which are incorporated herein by reference.

BRIEF SUMMARY OF THE INVENTION

The present invention provides apparatus and improved methods for mobilizing a uterus prior to a hysterectomy procedure, usually a transvaginal or a laparoscopic procedure. By "mobilizing," it is meant that the uterus is freed from surrounding tissue structures by severing and preferably cauterizing surrounding blood vessels, tubular structures, and ligaments. In the exemplary embodiments, severing and cauterizing is performed by a pair of opposed continuous loop electrodes which are introduced through the vaginal wall near the cervix and thereafter manipulated to surround the uterus. The continuous loop electrodes are then clamped together generally about the medial plane of the uterus so that the blood vessels, tubular structures, and ligaments are held therebetween. Radiofrequency or other energy is then applied through the continuous loop electrodes to sever and cauterize the blood vessels, tubular structures, and ligaments. After the uterus has been thus mobilized, the uterus may be withdrawn by conventional transvaginal or laparoscopic techniques. The methods and apparatus of the present invention would also be useful for mobilizing the uterus prior to conventional open laparoscopic hysterectomy procedures, but the advantages are more pronounced when performing transvaginal and laparoscopic procedures.

According to a first aspect of the present invention, an electrocautery device comprises a first continuous loop electrode and a second continuous loop electrode. The first and second loop electrodes are configured to be introduced to circumscribe the uterus, typically over the medial plane, and to clamp the blood vessels, tubular structures, and ligaments which extend laterally from the uterus to surrounding tissue structures. Once the blood vessels, tubular structures, and ligaments have been clamped, radiofrequency or other energy may be delivered through the electrodes to sever and cauterize the blood vessels, tubular structures, and ligaments. The radiofrequency is preferably bipolar but could in some instances also be monopolar. It may be desirable to alternately deliver both a cutting current and a coagulation current in order to first sever the blood vessels and thereafter to cauterize the severed blood vessels, tubular structures, and ligaments.

Apparatus according to the present invention will usually further comprise a coupling structure which anchors the loop electrodes, typically at one end, in a symmetric relationship. Usually, the coupling structure anchors the loop electrodes with an offset between the electrodes in the range from 0 cm to 5 cm, typically from 1 cm to 2 cm. Most often, the coupling structure will comprise a collar, where the electrodes may be fixed to the collar or may alternatively be slidable within apertures or channels in the collar to permit advancement of the electrodes relative to the collar.

Each of the continuous loop electrodes will usually be planar and have a generally oval shape with a length (when deployed) in the range from 20 cm to 50 cm, preferably from 20 cm to 30 cm, and a maximum width (when deployed) in the range from 5 cm to 25 cm. The loop geometry will preferably be oval, generally corresponding to the oval or pear shape of the uterus.

The loop electrodes will usually be insulated over those portions which are not intended to contact the blood vessels, tubular structures, ligaments, and other tissue which is being severed and cauterized. Thus, a proximal portion of each loop electrode will usually be insulated over those regions which will lie within the collar or other coupling structure when the loop electrodes are deployed. The back surfaces or sides of the loop electrodes, i.e. those which are facing away from the clamping side of the electrode, will also usually be insulated in order to avoid heating and damaging other tissues.

Each of the continuous loop electrodes will typically comprise or be formed from a resilient wire, where each resilient wire electrode is preferably laterally collapsible but relatively stiff in the anterior-posterior direction. This allows the loop electrodes to be laterally collapsed while being introduced through incisions in the vaginal wall prior to deployment around the uterus. The electrodes will then self-expand or otherwise be deployed to assume their shape which corresponds to the outer periphery of the uterus prior to clamping with the opposed electrode.

Preferred resilient wire geometries are asymmetric with a cross-section having an anterior-posterior dimension which is greater than a lateral dimension. Such asymmetric resilient wires may have a rectangular, oval, or other asymmetric cross-section. Alternatively or additionally, the resilient wire loop electrodes may be reinforced to increase stiffness in the anterior-posterior direction, either by electrically conductive or electrically non-conductive materials. In some instances, all or a portion of the insulation could also contribute to the desired stiffness in the anterior-posterior direction.

In a second aspect of the present invention, methods for mobilizing a uterus comprise positioning a first continuous loop electrode over lateral blood vessels, tubular structures, and ligaments attached to the uterus. A second continuous loop electrode may be simultaneously positioned beneath the lateral blood vessels, tubular structures, and ligaments, and the two loop electrodes clamped together to capture the blood vessels, tubular structures, and ligaments therebetween. Current is then delivered through or between the loop electrodes to sever and cauterize the blood vessels, tubular structures, and ligaments. The current is preferably radiofrequency, where it may be delivered bipolar between the two loop electrodes or monopolar using a separately applied dispersion electrode typically located on the patient's back or thighs.

Positioning of the loop electrodes typically comprises passing the loop electrodes transvaginally through incisions at the rear vaginal wall near the cervix. Usually, a pair of incisions will be made, one on top of the cervix (anteriorly) and one on the bottom of the cervix (posteriorly). The loop electrodes may then be advanced in a laterally collapsed configuration to pass through the incisions. The electrodes may then self expand or otherwise be deployed back to the original configuration after having passed through the incisions and having been positioned on either side of the uterus.

In specific aspects of the present invention, the electrodes may be advanced through a collar positioned adjacent to the cervix in the vaginal cavity. In such instances, the collar may define the lateral width of the electrodes as they pass through the incisions. Alternatively, the continuous loop electrodes may be constrained by an outer structure, such as a sheath, as they are being advanced through the incisions. In that case, the sheath or other constraining structure may be removed or released to allow the loops to deploy to their original configuration which has been sized to be placed about the uterus.

After the continuous wire loop electrodes have been properly positioned anteriorly and posteriorly of the blood vessels, tubular structures, and ligaments circumscribing the uterus, the power is delivered as discussed above in order to dissect and cauterize the blood vessels, tubular structures, and ligaments. It will then be necessary to remove the uterus by any one of several conventional or novel means. In some instances, it will be desirable to use the wire loop structures of the present invention to provide traction on the uterus and pull the uterus through the cervix and vagina. In some instances, the loop electrodes may be modified with inner barbs which engage and hold the uterus after it has been mobilized to facilitate extraction. Optionally, conventional forceps or other tools can be used in conjunction with the wire loop electrodes to assist in applying traction to remove the uterus.

In other instances, however, it may be desirable to remove the continuous wire loop electrodes prior to removing the uterus. In such instances, the uterus may then be removed transvaginally using other conventional techniques. Optionally, the mobilized uterus may be removed using a uterine traction device described in copending U.S. patent application Ser. No. 11/137,970, the full disclosure of which has previously been incorporated herein by reference. In still other instances, it may be desirable to remove the uterus laparoscopically where the uterus is usually morcelated using laparoscopically introduced morcelation tools. After morcelation, the uterus may be placed within a conventional removal bag and removed through a laparoscopic cannula.

BRIEF DESCRIPTION OF THE DRAWINGS

FIG. 3 illustrates an exemplary electrocautery device having first and second continuous loop electrodes constructed in accordance with the principles of the present invention.

FIGS. 3A-3C illustrate alternative cross sectional views of the loop electrodes taken at line 3-3 in FIG. 2.

FIGS. 4A and 4B illustrate a particular construction of the electrocautery device of FIG. 2, where the loop electrodes are axially slidable within a collar structure to facilitate deployment.

FIGS. 5A and 5B illustrate an alternative specific construction of the electrocautery device of FIG. 2 where the loop electrodes are constrained within a sheath to facilitate deployment.

DETAILED DESCRIPTION OF THE INVENTION

The present invention provides electrocautery devices and methods for use of such devices for mobilizing a uterus prior to hysterectomy. Devices and methods will be particularly suitable for use in both transvaginal and laparoscopic hysterectomy procedures, but could also find in more conventional, open surgical hysterectomy procedures. In addition to removal of the uterus in hysterectomy procedures, the devices and methods of the present invention could also be used for electrosurgical ligation of tubular structures, such as the ovaries (oophorectomy), and/or the fallopian tubes (salpingo-oophorectomy), the uterine arteries and the like.

Figure 1:
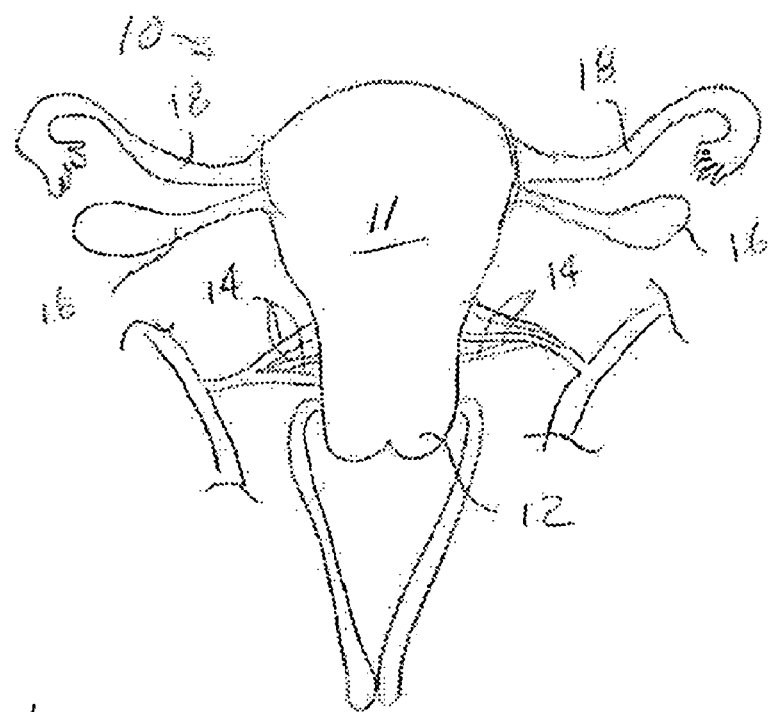
FIGS. 1 and 2 are simplified anterior-posterior and lateral views of a uterus, respectively, illustrating the connecting blood vessels and tubular structures.
Figure 2:
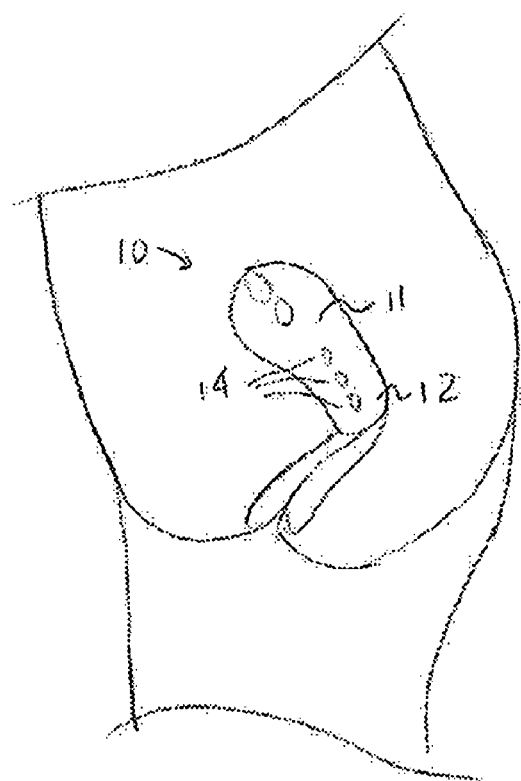

Referring to FIGS. 1 and 2, a uterus 10 comprises a uterine body 11 and a cervix 12. A number of structures, including uterine arteries 14, ovaries 16, and the fallopian tubes 18 are connected to the uterine body 11 around a generally circumferential line lying in a medial plane, i.e. a plane which is normal to the anterior-posterior direction through the patient. A number of ligaments, including the round ligaments, the uterosacral ligaments, the cardinal ligaments, and the like (not shown) are also attached to the uterine body 11 generally around the medial plane. The methods and apparatus of the present invention will provide generally for freeing the uterine body 11 from the surrounding blood vessels, tubular structures (fallopian tubes and ovaries), and ligaments which attach the uterine body to surrounding tissues. In addition, the uterine body 11 may be detached from the cervix 12 using conventional means other than the devices of the present invention. In other cases, however, it may be possible to modify the devices of the present invention so that they can also sever the uterine body 11 from the cervix 12 prior to hysterectomy or other procedures.

Referring now to FIG. 3, an electrocautery device 30 constructed in accordance with the principles of the present invention comprises a first continuous loop electrode 32 and a second continuous loop electrode 34. The first and second continuous loop electrodes 32 and 34 will have a peripheral geometry and dimensions selected to permit the electrodes to be introduced over and under a uterine body so that the electrodes may be clamped together to cut and cauterize blood vessels, tubular structures, ligaments, and the like, which surround the uterine body and connect the uterine body to surrounding tissues and blood supply. Thus, the loop electrodes 32 and 34 will generally have a pear-shape or similar ovoid configuration. The devices and electrode structures of the present invention may be provided in a plurality of particular shapes and sizes in order to conform to different patient anatomies, in which case a treating physician would select a particular shape and geometry to treat a patient based on prior imaging and analysis.

The first and second continuous loop electrodes 32 and 34 will usually, although not necessarily, be coupled together by a separate coupling structure, such as collar 36. Additionally, the loop electrodes 32 and 34 will be adapted to permit coupling to an external power supply 40, typically a radiofrequency power supply capable of delivering power in the range from 50 W to 1000 W, typically from 200 W to 500 W, usually in both cutting and coagulation modes, as is well known in the electrosurgical arts. The power supply 33 may be configured to deliver the radiofrequency energy in a "bipolar" manner, i.e. where the first and second loop electrodes 32 and 34 are connected to different poles of the power supply, respectively. Alternatively, the power supply 40 could be configured to drive the electrodes 32 and 34 in a "monopolar" manner, where the electrodes are connected to a common terminal of the power supply and a second terminal of the power supply is connected to a dispersive electrode which is externally connected to the patient (not shown) typically on the thighs or lower back.

Loop electrode structures according to the present invention are preferably constructed so that they are laterally flexible but relatively stiff in the anterior-posterior direction when they are introduced to the patient. Such preferential flexibility in the lateral direction allows the electrodes to be laterally constrained while they are being introduced, thus facilitating introduction through relatively small incisions in the vaginal wall, as will be described in more detail hereinbelow. Such preferential flexibility is typically achieved by constructing the loop electrodes to have a dimension in the anterior-posterior direction which is substantially greater than the lateral or width dimension of the electrode. Examples of such constructions are shown in FIGS. 3A-3C. For example, each electrode 32 and 34 may have a generally ovoid conductive body 40, preferably having a layer of insulation 42 on the side of the electrode which will not engage tissue when the electrodes 32 and 34 are clamped together. As shown in FIG. 3B, the electrodes could have a generally rectangular dimension with the greater dimension in the anterior-posterior direction and a layer of insulation 46 formed over the portion of the electrode 44 which is not engaging tissue. Finally, as shown in FIG. 3C, the electrode could comprise a circular structure 48 having a non-conductive backbone 50 to provide the preferential stiffness. It will be appreciated that many other specific configurations could also be utilized. Additionally, it will usually be desirable to insulate the entire electrode structure which is not expected to contact tissue for cutting or coagulation, generally being the structure which is in and around the collar 36.

A first method for deploying the loop electrodes 32 and 34 through the collar 36 is illustrated in FIGS. 4A and 4B. In this embodiment, the electrodes 32 and 34 (with only 32 being illustrated) are axially slidable within apertures or channels formed in the collar 36. Thus, prior to deployment, the electrodes 32 and 34 may be drawn proximally so that only a small portion of the loop lies distal to the collar. After the collar is placed near the cervix (as described in more detail below) the electrodes 32 and 34 may be advanced distally forward, as shown in broken line in FIG. 4A, until they are fully deployed, as shown in FIG. 4B.

Optionally, a plurality of barbs 37 may be formed over at least a portion of an interior edge 39 of either or both of the loop electrodes 32 and 34. The barbs will engage and grasp the uterine body to assist in removing the mobilized uterine body by pulling on the electrodes. For example, after applying energy to cauterize and cut the blood vessels, tubular structures, and ligaments, the loop electrodes can be circumferentially tightened about the uterine body. The barbs will penetrate the uterine tissue to help hold the uterine body as it is extracted.

As an alternative to deploying the electrode structure through the collar as shown in FIGS. 4A and 4B, the electrode structures could be fixed within the collar 36 and constrained in sheath structures 60, as shown in FIGS. 5A and 5B. FIG. 5A is a side view showing both electrodes 32 and 34, while FIG. 5B is a top view illustrating only electrode 32 as constrained within the collar 60. The embodiment of FIGS. 5A and 5B may thus be introduced to the patient by advancing the sheathed electrodes 32 and 34 through incisions through the vaginal wall adjacent the cervix, with one electrode passing over the uterine body (anteriorly) and the other electrode passing beneath the uterine body (posteriorly). After the electrodes 32 and 34 have been properly positioned, the sheaths 60 may be withdrawn proximally, allowing the electrodes to resume their deployed configurations, as illustrated by electrode 32 shown in broken line in FIG. B.

Figure 6:
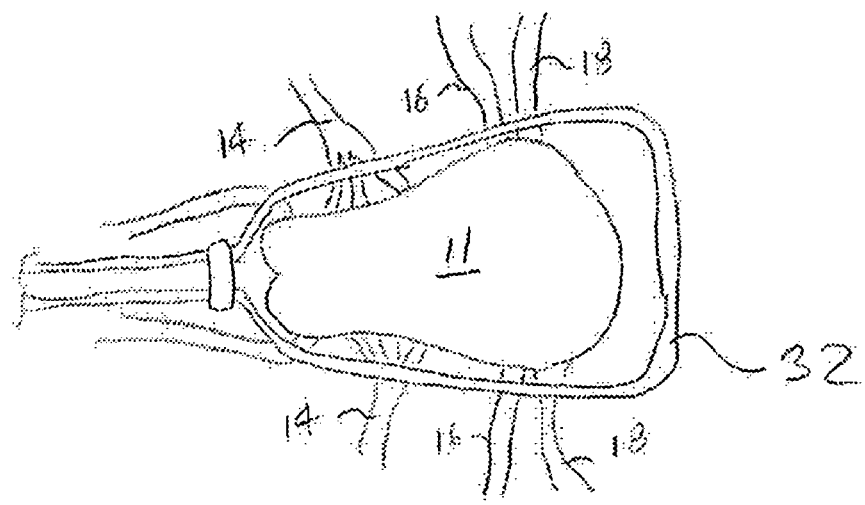
FIGS. 6, 7A, and 7B illustrate use of the electrocautery device of FIG. 2 for mobilizing a uterus by cutting and cauterizing the connecting blood vessels, tubular structures, and ligaments, in accordance with the principles of the present invention.
Figure 7A:
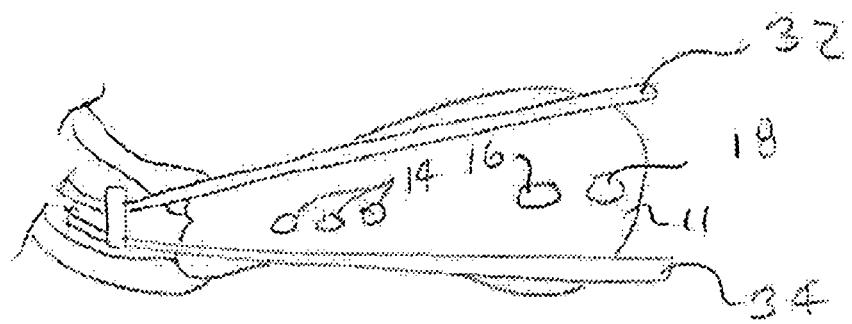
Figure 7B:
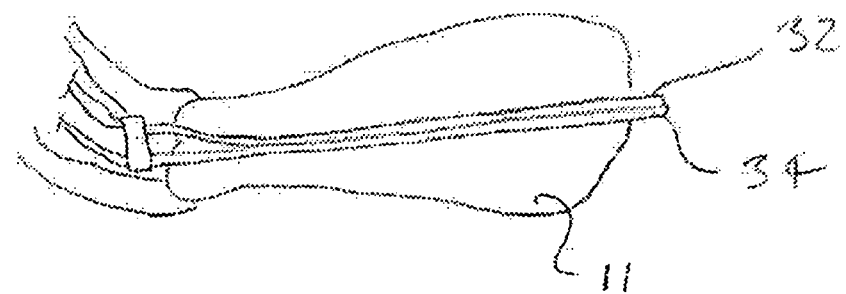

Referring now to FIGS. 6, 7A, and 7B, deployment of the electrocautery device of the present invention for cutting and cauterizing structures surrounding uterine body 11 to mobilize the uterus prior to hysterectomy are described.

The continuous loop electrodes 32 and 34 are first deployed through incisions in the vaginal wall, typically near the cervix and above and below (anterior and posterior) of the uterine body 11. The loop electrode structures are advanced to positions over and beneath the uterine body 11, as shown in FIGS. 6 and 7A, by either of the techniques described above in connection with the device embodiments of FIGS. 4A and 4B and FIGS. 5A and 5B. The continuous loop electrode structures 32 and 34 are clamped together as shown in FIG. 7B, and radiofrequency or other power provided to the electrode structures in order to first cut and subsequently or simultaneously cauterize the various surrounding structures, including tubular structures, blood vessels, ligaments, and the like.

Once the surrounding structures have been cauterized and severed, the uterus may be removed by conventional techniques, typically by transvaginal or laparoscopic techniques. Transvaginal removal may be assisted using the methods and has been previously incorporated herein by reference. Usually, the cervix will be removed together with the remaining portions of the uterine body. In other instances, however, it may be desired to preserve the cervix. In such instances, the loop electrodes may be modified so that they do not cut or cauterize arteries and veins with supply blood to the cervix.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for mobilizing a uterus, said method comprising:
   positioning a first continuous loop electrode having a pear-shaped or ovoid configuration over lateral blood vessels, tubes, and ligaments attached to the uterus;
   positioning a second continuous loop electrode having a pear-shaped or ovoid configuration beneath the lateral blood vessels, tubes, and ligaments;
   clamping the first and second loop electrodes together to capture the blood vessels, loops, and ligaments therebetween; and
   delivering current through or between the loop electrodes to sever and cauterize the blood vessels, tubular structures, and ligaments.

2. A method as in claim 1, wherein positioning the loop electrodes comprises passing the loop electrodes transvaginally through incisions in the rear vaginal well near the cervix.

3. A method as in claim 2, wherein the loop electrodes are laterally collapsed as they pass through the incisions.

4. A method as in claim 3, wherein the electrodes are advanced through a collar positioned adjacent the cervix, wherein the collar defines the lateral width of the loop electrodes as they pass through the incisions.

5. A method as in claim 3, wherein the loop electrodes are constrained by an outer structure when advanced through the incisions, further comprising releasing the loop electrodes from constraint to deploy the loop electrodes about the uterus.

6. A method as in claim 1, further comprising dissecting the cervix and removing the uterus.

7. A method as in claim 6, wherein the uterus is removed through the vagina.

8. A method as in claim 7, wherein the uterus is removed by pulling on the loop electrodes which provide at least a portion of the traction for pulling the uterus through the cervix.

9. A method as in claim 8, wherein an inner edge of at least one of the loop electrodes grasps the uterus while traction is applied.

10. A method as in claim 9, wherein grasping comprises penetrating barbs on the loop electrode into the uterine body.

11. A method as in claim 7, wherein the uterus is removed by engaging the uterus with forceps and pulling on the forceps to provide at least a portion of the traction for pulling the uterus through the cervix.

12. A method as in claim 6, wherein the uterus is removed through an abdominal incision.

13. A method as in claim 12, wherein the uterus is first morcellated and then removed through a cannula positioned in the abdominal incision.

* * * * *